(12) United States Patent
Miller et al.

(10) Patent No.: US 6,423,193 B1
(45) Date of Patent: Jul. 23, 2002

(54) NITROGEN DOPED CARBON ELECTRODES

(75) Inventors: Barry Miller, Bratenahl, OH (US); Rafi Kalish, Haifa (IL); Xu Shi, Singapore (SG)

(73) Assignee: Case Western Reserve University, Cleveland, OH (US)

( * ) Notice: Subject to any disclaimer, the term of this patent is extended or adjusted under 35 U.S.C. 154(b) by 0 days.

(21) Appl. No.: 09/385,233

(22) Filed: Aug. 30, 1999

(51) Int. Cl.$^7$ .............................. C25B 9/00; C25C 7/00; C25D 17/00
(52) U.S. Cl. ............. 204/242; 204/290.01; 204/290.15; 204/294
(58) Field of Search ........................... 204/242, 290.01, 204/290.15, 294

(56) References Cited

U.S. PATENT DOCUMENTS

| | | | | | |
|---|---|---|---|---|---|
| 4,511,442 A | * | 4/1985 | Pellegri | ........................ | 205/501 |
| 5,013,139 A | * | 5/1991 | Kaganowicz et al. | ........ | 349/125 |
| 5,607,770 A | * | 3/1997 | Lewis et al. | ................. | 428/408 |
| 5,690,901 A | * | 11/1997 | Zhang et al. | ............ | 423/449.6 |
| 6,168,694 B1 | * | 1/2001 | Huang et al. | ........... | 204/290.12 |

OTHER PUBLICATIONS

Takahashi et al.(Effect of target temperature during nitrogen ion implantation on electrochemical properties of ion–implanted glassy carbon; Journal of Electroanalytical Chemistry, vol.: 396, Issue: 1–2, Oct. 31, 1995).*

L.K. Cheah et al., "Properties of Nitrogen Doped Tetrahedral Amorphous Carbon Films Prepared by Filtered Cathodic Vacuum Arc Technique," Journal of Non–Crystalline Solids, pp. 1–9. Dec.1 ,1998.

L.K. Cheah et al., "Nitrogenated Tetrahedral Amorphous Carbon Films Prepared by Ion–beam–assisted Filtered Cathodic Vacuum Arc Technique for Solar Cells Application," Appl. Phys. Lett., vol. 73, No. 17, pp. 2473–2475 (Oct. 1998).

L.K. Cheah et al., "Field Emission from Undoped and Nitrogen–doped Tetrahedral Amorphous Carbon Film Prepared by Filtered Cathodic Vacuum Arc Technique," Diamond and Related Materials 7, pp 640–644. Dec. 1, 1988.

* cited by examiner

Primary Examiner—Bruce F. Bell
Assistant Examiner—Wesley A. Nicolas
(74) Attorney, Agent, or Firm—Fay, Sharpe, Fagan, Minnich & McKee, LLP

(57) ABSTRACT

An electrode (22) formed from a layer (24) of tetrahedral carbon doped with nitrogen (taC:N) has both electroanalytical and electrosynthetic applications. The electrode includes a substrate material (26), such as a silicon wafer, for supporting the taC:N layer. The electrode has good durability under a high anodic potential and high selectivity for conversion of chloride ions to chlorine, and for other electron transfer reactions. The electrode is readily formed at ambient temperatures by vacuum deposition of carbon and nitrogen ions on to the substrate. Masking of the substrate during deposition allows the formation of microelectrode arrays.

12 Claims, 7 Drawing Sheets

NITROGEN DOPED CARBON ELECTRODES

BACKGROUND OF THE INVENTION

The present invention relates to the electrochemical arts. It finds particular application in conjunction with an electrode material for electrosynthesis and analysis and will be described with particular reference thereto. It should be appreciated, however, that the invention is also applicable to a variety of applications where electrical conductivity or chemical selectivity are desired.

Electrodes formed from electrically conductive diamond have been used in a number of applications. The diamonds are commonly of two types, namely, implanted diamonds having their surface conductivity from damage-generated $sp^2$ (graphitic) content and chemically-vapor deposited boron-doped thin p-type diamond films of virtually metallic conductivity produced at high substrate temperatures.

The latter films have shown a wide electrochemical window for aqueous systems combined with the chemical resistance properties of diamond. The boron-doped diamond films, however, require high temperatures for their formation (typically 1175 K) and relatively small coating areas are presently available. Additionally, no significant degree of electrocatalytic activity is shown by the hydrogen terminated, inert surface of the boron-doped films, which makes all but outer-sphere electron transfer slow.

The present invention provides a new and improved electrode which overcomes the above-referenced problems and others.

SUMMARY OF THE INVENTION

In accordance with one aspect of the present invention, an electrochemical system is provided. The system includes an electrode comprising a substrate, and a layer of a material on the substrate, the layer consisting essentially of carbon incorporating nitrogen. The system also includes an electrolyte and a counter electrode.

In accordance with another aspect of the present invention, a method of electrochemical synthesis of a product of a redox reaction is provided. The method includes providing an electrode from a layer of a material consisting essentially of carbon incorporating nitrogen and inserting the electrode in an aqueous solution in which the redox reaction takes place. The method further includes passing an electric charge through the electrode.

In accordance with another aspect of the present invention, a method of forming an electrochemical system is provided. The method includes forming an electrode from a substrate with a layer of a nitrogen-containing amorphous carbon thereon and separating the electrode and a counter electrode with an electrolyte.

In accordance with another aspect of the present invention, a method of detecting a product of a chemical reaction is provided. The method includes providing a sensor with a wide electrochemical window between hydrogen and oxygen evolution potentials, the sensor including a carbon and nitrogen amorphous layer. The method further includes measuring a flow of current at a potential within the electrochemical window, the potential selected to correspond to a potential at which the chemical reaction takes place and determining a concentration of the product from the current measured.

One advantage of the present invention is that electrode material may be prepared at ambient temperatures.

Another advantage of the present invention is the provision of a sensor which has a wide potential window.

Another advantage of the present invention is the provision of an electrode which exhibits reversible behavior with outer sphere couples.

Another advantage of the present invention is the provision of a sensor which combines high catalytic ability with a high durability.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

DETAILED DESCRIPTION OF THE PREFERRED EMBODIMENTS

Figure 1:
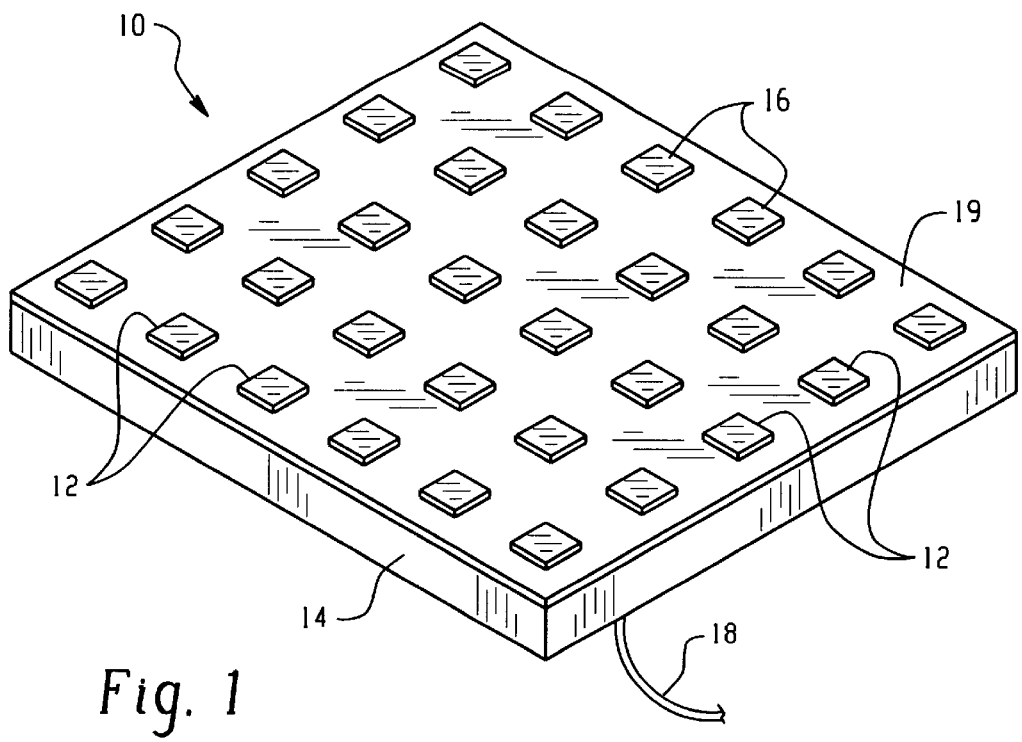
FIG. 1 is a perspective view of a first embodiment of an electrode according to the present invention.
Figure 2:
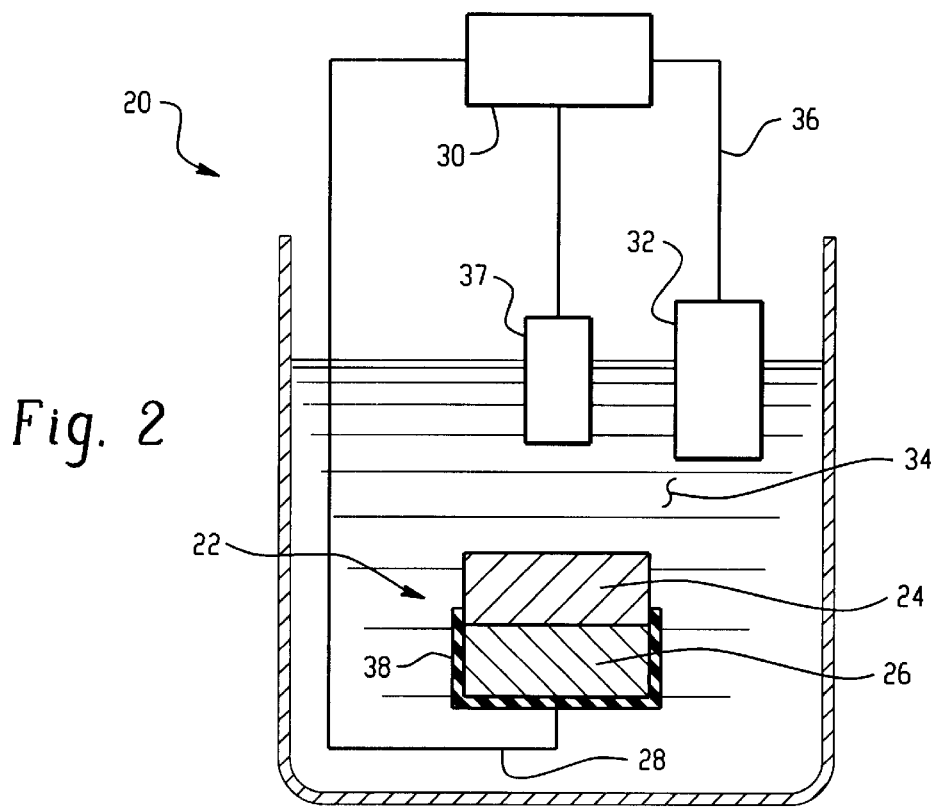
FIG. 2 is a perspective view of an electrochemical cell with a second embodiment of an electrode according to the present invention.

A nitrogen-incorporated tetrahedral amorphous carbon material is used to form electrodes for a variety of electroanalytical and electrosynthetic applications. With reference to FIG. 1, one embodiment of an electrode 10 includes a film or layer 12 of the nitrogen-incorporated tetrahedral amorphous carbon (taC:N) deposited on a substrate 14. In the electrode 10 of FIG. 1, the layer 12 is deposited in the form of an array 16 of microelectrodes, each microelectrode 12 being electrically connected to an electrical lead 18 via the substrate but insulated from each of the other microelectrodes by an insulating layer 19 on the surface of the substrate. A wide variety of other configurations of the layer, such as a uniform sheet, as shown in FIG. 2, are also contemplated. The electrical lead 18 connects the layer 12 or microelectrodes through an ohmic contact to the substrate 14 to electrical equipment, such as a source of potential, current, or monitoring equipment (not shown).

The substrate functions as a support for the layer 12 and is preferably also conductive. The substrate can be formed of a variety of materials, including metals, plastics, and silicon wafer materials. Silicon wafers are preferred substrate materials because of their smooth surfaces which allow the deposition of thin, coherent, pore-free films, and because their surface layers can be converted to inert silicon dioxide on contact with water. In the embodiment of FIG. 1, for example, the surface layer 19 of the substrate is preferably silicon dioxide, which provides an insulation between each of the microelectrodes 17, while the underlying silicon substrate is conductive, allowing current to pass therethrough, to or from the microelectrodes.

Where the substrate is non conductive, electrical leads are connected directly with the layer 12 of taC:N.

With reference to FIG. 2 an electrochemical system 20 incorporates a taC:N electrode 22. The electrode 22 is similar to the electrode of FIG. 1 except in that a uniform layer of taC:N 24 is in ohmic contact with an underlying conductive substrate 26. An electrical lead 28 connects the substrate to electrical equipment 30.

A counter electrode 32 is separated from the taC:N electrode 22 by an electrolyte 34. A second electrical lead 36 connects the counter electrode with the electrical equipment 30. Preferably, an insulating material 38, such as a layer of epoxy, insulates the substrate from the surrounding electrolyte.

The choice of materials for the counter electrode and electrolyte are dependent on the selected function of the cell, as will be described in further detail below. The electrolyte may be liquid or solid. It preferably comprises an aqueous solution of an acid or a base for conducting current between the electrode 22 and the counter electrode 32, although non-aqueous electrolytes are also contemplated. The electrolyte also acts as a medium for dissolved chemicals which are to undergo a reaction at the surface of the electrode.

The choice of electrical equipment 30 also depends on the selected function of the electrode, as is known in the art, but typically comprises electrochemical monitoring equipment when the electrode is used as a sensor for electroanalytical applications. For electrosynthetic applications, the electrical equipment applies a potential between the taC:N electrode 22 and the counter electrode 32. A third electrode, such as a saturated calomel reference electrode 37, may also be employed in the system 20, as is known in the art.

Figure 3:
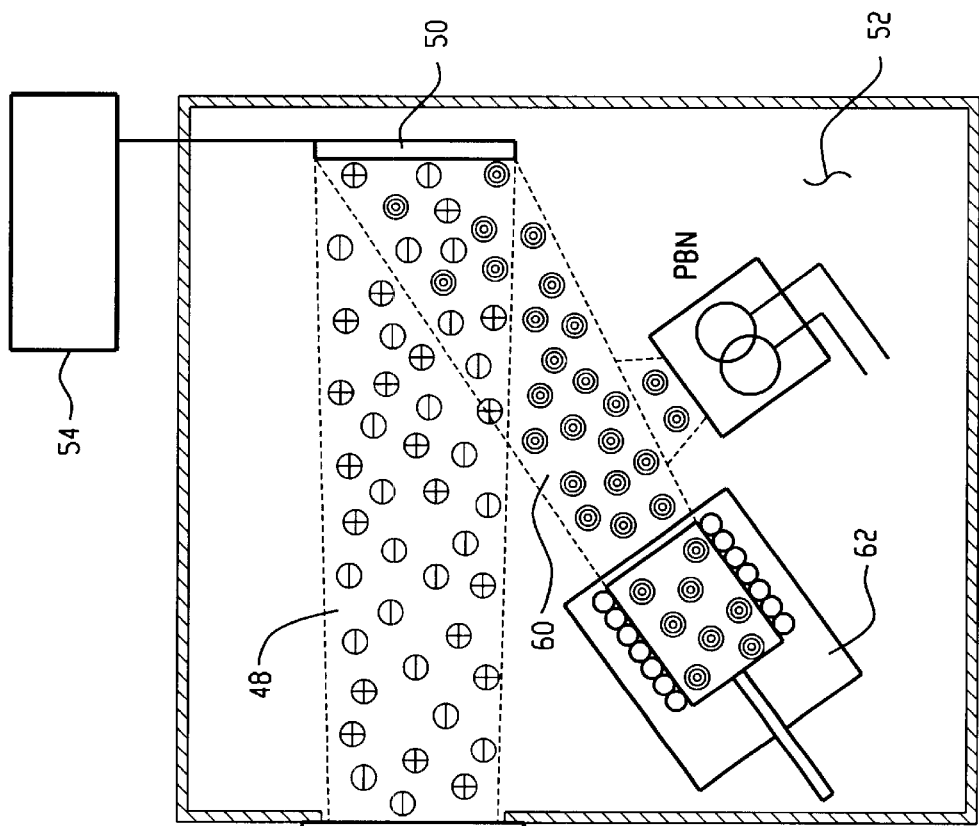
FIG. 3 is a schematic diagram of a system for preparing electrode materials according to the present invention.
Figure 3:
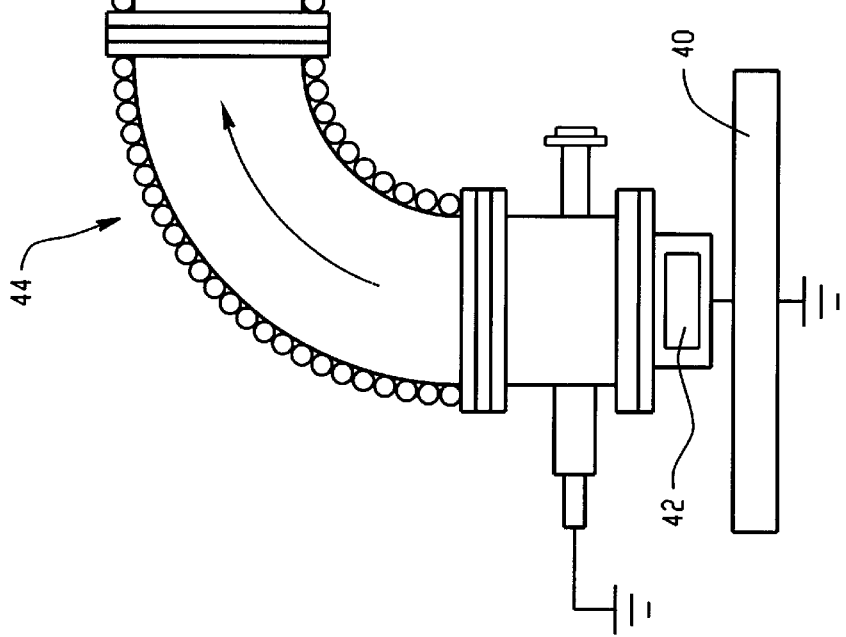

With reference also to FIG. 3, the layer of taC:N may be deposited on the substrate by a variety of deposition techniques. FIG. 3 illustrates one preferred technique, which employs a filtered vacuum arc (FCVA). A charged beam of carbon ions is generated by a vacuum arc supply 40 from a graphite target 42 by laser ablation, passage of an arc between two electrodes, use of a heated filament, or other suitable methods of generation. The carbon ions are energy selected and filtered by a magnetic sector 44 to remove particulates, and the resulting carbon plasma beam 48 is directed at a sheet 50 of the substrate material positioned within an evacuated chamber 52. The sheet is held at a selected potential by a substrate bias 54. One suitable substrate material is a $p^{++}$ Si<100> substrate having a resistivity of about 0.03 ohm-cm.

A beam 60 of nitrogen ions is produced by an ion beam source 62 and is directed at the substrate sheet. The beams of carbon and nitrogen ions are simultaneously incident on the substrate sheet 50, and combine to form a film of taC:N on the substrate sheet. The film thus formed is glassy and is of near atomical smoothness (as atomically smooth as the underlying silicon) and of less than 0.1 micrometers in thickness. Optionally, one or other of the beams is switched on before the other or switched off before the other, to influence the properties of the innermost layer or outermost layer of the film, respectively. The sheet can then be sectioned as desired to form electrodes 12, 22 of varying configurations. Nitrogen concentrations of the films vary, depending upon the flow rate of nitrogen ions, from about 2 atomic % at a flow rate of 0.2 sccm up to about 12 atomic % at a flow rate of around 12 sccm.

In an alternative method of preparing the film, a single beam of nitrogen and carbon ions is directed at the substrate sheet 50. The single beam may be formed, for example, by generating carbon ions from a suitable source in an atmosphere containing nitrogen. For example, a carbon arc is used in a nitrogen atmosphere to generate both nitrogen and carbon ions. These are passed together through a magnetic sector for filtering out unwanted carbon particles. The remaining plasma beam of carbon and nitrogen ions forms the taC:N layer as it impinges on the substrate material. This method is particularly suited to forming taC:N layers with relatively high nitrogen contents (e.g., about 15–18% nitrogen).

The chamber 52 and substrate material 50 need not be heated for deposition of the taC:N film 12, 24, in either method. The films are readily formed at ambient temperatures, typically at around 18–30° C., although they can be formed at higher or lower temperatures, from about 0–100° C. At temperatures lower than about 18° C., an accelerating voltage may be needed to form the film. An advantage of working at low temperatures (at around ambient and below) is that the resulting film is highly amorphous with a glassy structure and has few of the grain boundaries which are an unavoidable result in boron doped carbon films, which must be formed at higher temperatures (typically 1175 K). Particularly preferred deposition temperatures are around 20–25° C.

The films formed by this method have an atomic ratio of from about 70/30 $sp^3/sp^2$ carbon up to close to 85/15 $sp^3/sp^2$ carbon (the atomic ratio for carbon without nitrogen), depending on the nitrogen concentration of the taC:N. The high $sp^3$ (tetrahedral carbon) content of the film gives the film a high stability which is not readily degraded. This compares very favorably with pure carbon films, which tend to be consumed during anodic use.

Preferably, the nitrogen content of the film is from about 2–30 atomic percent nitrogen. If the nitrogen concentration of the film is too low, then the P-type character of the carbon is counterbalanced by the N-type character of the nitrogen (holes and electrons compensate for one another) resulting in an increase in the resistivity of the film. More preferred nitrogen concentrations for the layer 12 are about 5–15 atomic %, with a particularly preferred nitrogen concentration of 8–12 atomic %. Since electrochemical reactions take place on the surface of the film, the film can be of different nitrogen concentrations throughout its depth. For example, the below surface concentration could be lower or higher than the surface nitrogen concentration as long as the conductivity of the film is not adversely affected.

The films can be formed of virtually any desired thickness. Preferably the thickness is in the range of from that required to provide coherent and pore free coverage of the substrate material, which may occur at around 10 nanometers (100 Å) thickness for silicon wafer substrates (or as little as 1 nanometer if the substrate is particularly smooth and the layer evenly deposited), up to about 70 nanometers, or more. At higher thicknesses, there may be a tendency for the film to disbond due to internal stresses. A preferred film thickness for use in sensors is 30–70 nanometers, more preferably 30–50 nanometers, most preferably about 40 nanometers.

For thicknesses in the 30–100 nanometer range, the taC:N films have a resistivity of from about 10 to $10^3$ ohm-cm. Although this resistivity is relatively high, the low thickness of the films ensures that the overall resistance of the film is low. For example, in films of about 40 nanometers thickness and 1 $cm^2$ in area, this results in a resistance of $4 \times 10^{-3}$ ohms when the resistivity is $10^3$ ohm-cm. (Resistance=(resistivity×thickness)/area). This resistance is at least a few orders of magnitude less than cell uncompensated solution resistances. Accordingly, the resistivity of the taC:N film is sufficiently low that it does not affect the overall resistance of an electrochemical system incorporating the electrode.

Band gaps (the energy required to excite an electron from the valence band to the semiconductor conduction band) for the taC:N films are advantageously low, around 2.5–2.7 eV, as compared with around 5.5 eV for natural diamond and about 1.1 for silicon. This allows the material to be used as a window layer in, for example, solar cells. At nitrogen contents of around 8%, the taC:N material behaves metallically (ohmically), passing current in either direction, without the need for rectification.

Because of the low temperatures used in formation, the taC:N electrode is conveniently formed in a variety of configurations. For example, during deposition, the substrate surface can be masked prior to deposition to define an electrode comprising an array 16 of microelectrodes, as shown in FIG. 1, and the mask material removed after deposition to reveal the silicon substrate in between the microelectrodes. Lithographic deposition, or other techniques, may be used for masking the silicon substrate surface prior to deposition of the taC:N layer 12. The mask material is then removed. The exposed silicon is converted to inert silicon dioxide once the electrode is immersed in water. This allows the electrode to be used in integrated circuits, microelectrochemical devices, and the like. Such masking is not feasible at the high temperatures needed for forming boron-doped carbon films. The taC:N layer 12 can also be laid down in other electrode shapes, such as rings or disks. Alternatively, the substrate sheet coated with the film can be cut into desired shapes and used in the preparation of rotating disk electrodes (RDE), rotating ring disk electrodes (RRDE), and the like.

taC:N electrodes formed as described herein have been found to possess the following unexpected and desirable characteristics:

(1) taC:N electrodes show a wider potential window in aqueous systems than for boron-doped diamond. By potential window, it is meant the region between the potential at which an anodic reaction takes place and the potential at which a cathodic reaction takes place for the electrolyte. For example, the potential window between hydrogen and oxygen evolution is larger for taC:N than for B-diamond. This creates a greater window in which other reactions can take place in aqueous solution without resulting in significant evolution of hydrogen or oxygen. Currents for these other reactions can also be measured without influence of anodic and cathodic currents of the electrolyte. In terms of hydrogen-oxygen windows or hydrogen-metal oxidation windows, taC:N also compares favorably with other known electrode materials. For example, potential windows obtained with platinum and mercury under similar conditions are smaller than those obtained for taC:N.

(2) The smooth taC:N interfaces have reduced surface areas, resulting in a lower capacitative current and show less noise than boron-doped diamond, due to their smoothness and lack of grain boundaries;

(3) taC:N electrodes show reversible behavior with outer sphere electron transfer couples (electrochemical reactions between two species which differ in the number of electrons and differ little in structure, such as $Ru(NH_3)_6^{3+}$ and $Ru(NH_3)_6^{2+}$). The taC:N electrode readily passes electrons between the species.

(4) taC:N electrodes show good electron transfer kinetics-intermediate between polished pyrolytic graphite (excellent) and boron-doped diamond for the quinone/hydroquinone couple and other catechol derivatives. The electrodes have excellent analytical behavior because of the uniform surface and larger potential window. These properties make the electrode a good sensor for dopamine and other neurotransmitters.

(5) taC:N electrodes show considerably higher catalytic activity for $Cl_2/Cl^-$ than boron-doped diamond.

(6) taC:N electrodes have very high durability under a high anodic potential. The taC:N electrode compares very favorably with conventional graphite anodes. This, and other properties of the electrode allow it to function efficiently in the oxidation of organic and inorganic materials, which may have uses, for example, in the clean-up of contaminated water (by oxidation of organic chemicals) and in the manufacture of ozone.

The above examples of the unexpectedly high catalytic activity and efficient electrochemical behavior demonstrate the variety of applications for electrodes formed from taC:N for both electroanalytical (detection) and electrosynthetic (catalytic) purposes. These properties may be due, in part, to the π-bonding from the $sp^2$ characteristics of some of the taC:N carbon and the electrons available from the nitrogen lone pair. When combined with the advantage of ready deposition at ambient temperatures, which widens the possibilities for electronics and for convenient masking to fabricate, for example, microelectrode arrays and sensors, the electrochemical properties of taC:N sensors are broad and unexpected.

Without intending to limit the invention, the following Examples illustrate the variety of electron transfer kinetics possible with the electrode material.

EXAMPLE 1

Cyclic Voltammetry Studies of Electron Transfer by tac:N in Comparison with Boron-Doped Diamond With reference once more to FIG. 2, the electrochemical behavior of the taC:N electrodes towards outer sphere reversible couples was compared with that of highly boron-doped diamond electrodes (>1000 ppm B). In all the plots shown herein, positive currents (greater than zero) indicate anodic, oxidation reactions are taking place, while negative currents indicate that cathodic, reduction reactions are taking place.

A taC:N coated Si wafer was prepared as described above by the dual beam method, with the taC:N forming a uniform layer 24 on the silicon substrate 26 of about 40 nm in thickness. The boron-doped diamond ("B-diamond") electrodes were prepared by chemical vapor deposition of boron and carbon onto a silicon wafer at high temperature to a similar thickness. Disks 22 of the taC:N and boron-doped diamond on silicon were prepared for cyclic voltammetry (stationary electrode) studies by fracturing the coated substrates into rectangles and then abrasively shaping these into disks, although rectangles can also be used.

Saturated calomel reference electrodes (SCE) 37 and carbon rod counter electrodes 32 were employed in the studies. Reagent grade chemicals and distilled water further purified with a Barnstead Easy Pure UV water system were used, with nitrogen purge gas in the cell as required.

A Pine AFCBP1 bipotentiostat with a computerized data acquisition and programming system 30 was generally used for applying voltages and taking measurements. The studies were carried out in a 1 mM $Ru(NH_3)_6Cl_3$ and 1 mM Co(III)-sepulchrate in 1M KCl electrolyte solution 34. The scan rate was 50 mV/s.

Figure 4:
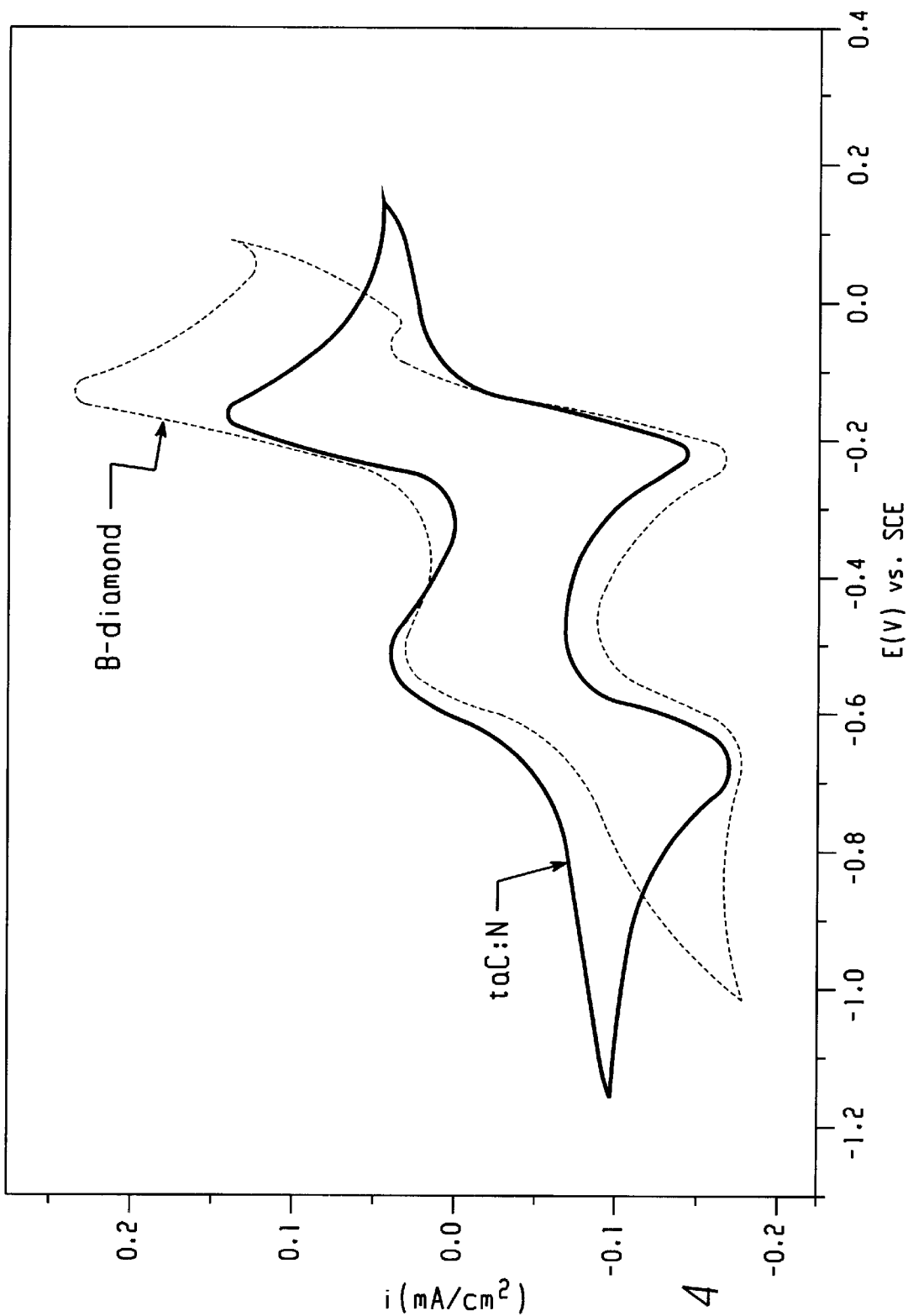
FIG. 4 is a cyclic voltammogram for stationary nitrogen incorporated tetrahedral amorphous carbon (taC:N) and boron doped diamond (B-diamond) disks in a solution comprising 1 mM $Ru(NH_3)_6Cl_3$, 1 mM Co(III)-sepulchrate, and 1M KCl at a scan rate of 50 mV/s.

The response to outer sphere couples in cyclic voltammetry is shown in FIG. 4. Current density refers to the projected area of the electrode. The cyclic voltammograms thereshown indicate that the electron transfer to a solution both containing $Ru(NH_3)_6^{+3}$ and co(III)-sepulchrate at taC:N is at least as kinetically reversible as that of the highly doped boron diamond film. This can be seen from the peak shape and near Nernstian separation of the peak and trough in both cases. As shown in FIG. 4, for example, troughs for taC:N and B-diamond both occur at about −0.2V vs SCE, and the corresponding peaks at less than −0.1V vs SCE, giving a peak separation of less than 0.1V in each case.

For both materials, other experiments have shown that lower dopant concentrations (N and B concentrations, respectively) show increasing peak separation, particularly in the case of B-diamond. At very low dopant concentrations, both materials begin to function as semiconductors, making them less suited to carrying out oxidation/reduction reactions on their surfaces. Slightly higher peaks in cyclic voltammetry and more sloped baselines for the much rougher, faceted boron-doped diamond are also visible in FIG. 4.

EXAMPLE 2

Rotating Disk Studies of Proton/Electron Transfer by taC:N Electrodes in Quinone/Hydroquinone solutions Rotating disk electrode (RDE) studies compared the taC:N electrode wit h graphite and boron-doped diamond electrodes. The results show the higher reaction rates of the taC:N electrode and thus its suitability as a fast proton/electron transfer system.

Quinone (obtained from MC&B) and hydroquinone (obtained from Eastman) were recrystallized from ethanol. A Pine MSRX controller and rotator were employed for the RDE experiments. The electrode materials were formed from taC:N coated and boron-doped diamond coated silicon, as described for Example 1, and abrasively shaped into disks for the RDE experiments. The behavior of a mechanically polished pyrolytic graphite (PG) RDE gave an example of highly active carbon for reference.

Figure 5:
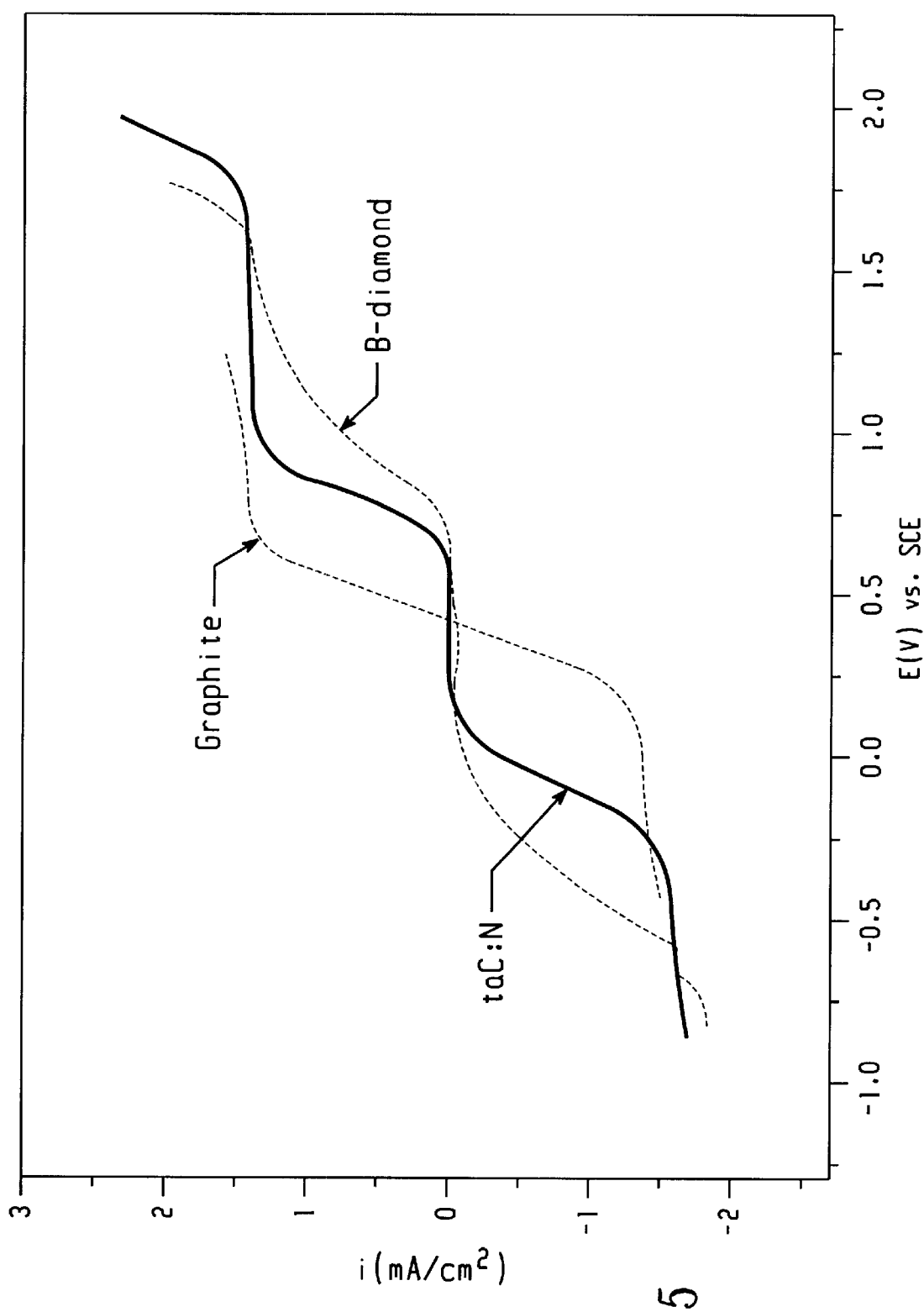
FIG. 5 is a plot of rotating disk electrode scans for electrodes of taC:N, carbon, and B-diamond, in a solution comprising 1 mM hydroquinone/1 mM quinone and 1M $HClO_4$ at a scan rate of 10 mV/s, and rotation speed of 1600 rpm.

FIG. 5 is a plot of RDE scans of the three electrodes, as marked, in an aqueous solution of 1 mM hydroquinone/1 mM quinone in an electrolyte of 1M $HClO_4$. The scan rate was 10 mV/s and the rotation speed was 1600 rpm for each electrode.

The results of this, and other experiments show that electron transfer kinetics for boron-doped diamond are universally slow for any reactions in which surface interactions are required. This is clearly indicated for hydroquinone/quinone in 1M acid. As shown in FIG. 5, the wave for B-diamond is severely split, as compared to the well-defined composite wave produced at graphite surfaces, such as the mechanically polished PG disk. The composite wave for taC:N is split much less than for B-diamond and, in clear contrast, the wave is excellently developed. This is partly due to the smoothness of the taC:N electrode, provided by the amorphous, grain boundary-free nature of the taC:N film and partly due to the wider electrochemical window between hydrogen evolution and oxygen evolution in 1M $HClO_4$.

EXAMPLE 3

Hydrogen and Oxygen Evolution at taC:N and B-Diamond Electrodes

These experiments further demonstrate the wider electrochemical window between hydrogen evolution and oxygen evolution of taC:N as compared with B-diamond. Cyclic voltammograms for stationary B-diamond disks and taC:N disks in 1M $HClO_4$ (FIG. 6A) and 2M HCl (FIG. 6B) were obtained. The disks were prepared as for Example 1. A Pine MSRX controller was employed for the experiments. Scan rates of 100 mV/s were used for both experiments. Directions of sweep were as shown by the arrows.

Figure 6A:
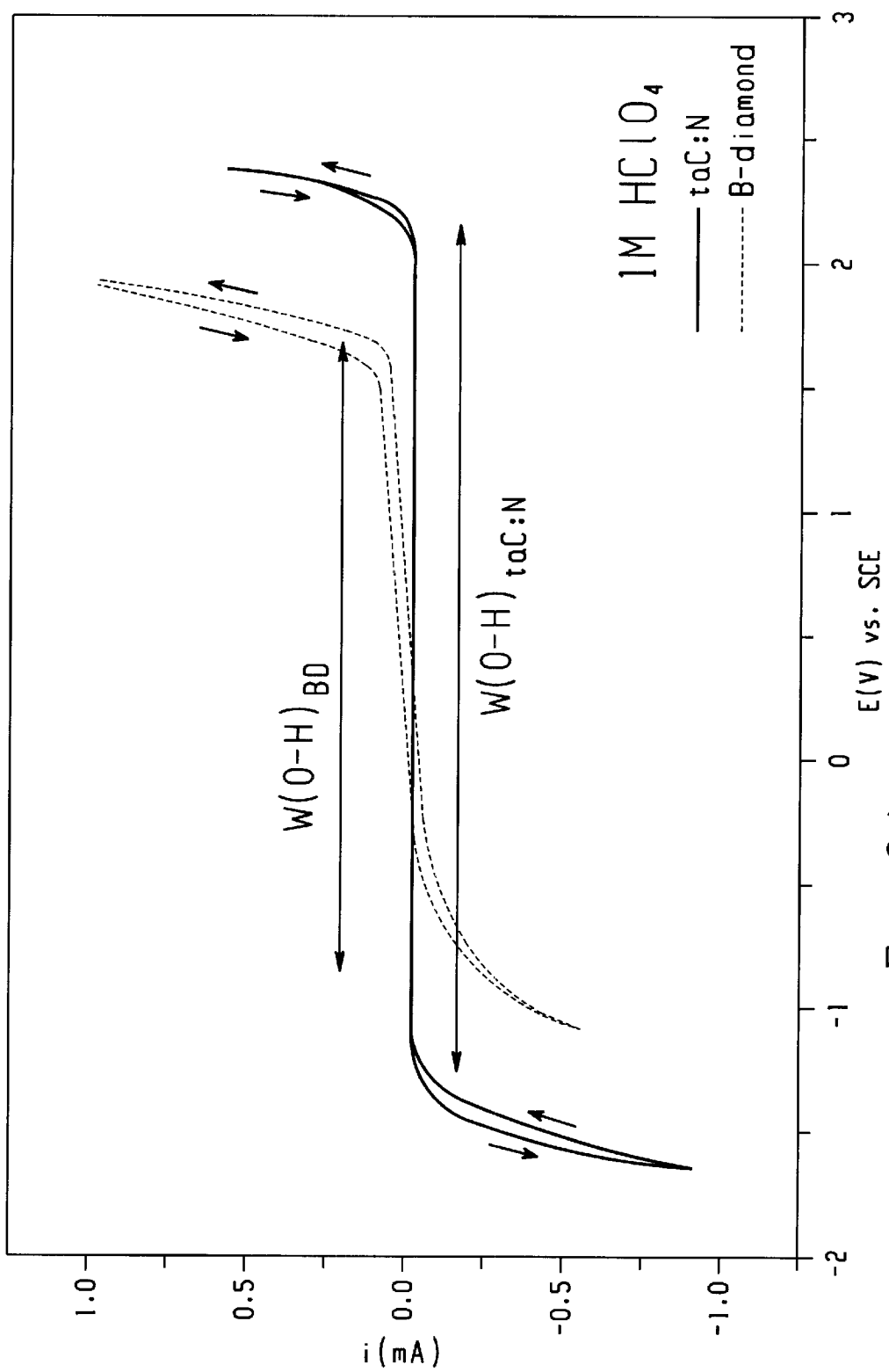
FIG. 6A is a plot of a cyclic voltammogram for stationary B-diamond disks in 1M $HClO_4$ at a scan rate 100 mV/s in the directions of sweep shown.

FIG. 6A shows that the potentials for hydrogen and oxygen evolution (lower left and upper right of each curve, respectively) are both qualitatively greater (with respect to an SCE base line of 0 volts) for taC:N than for the B-diamond and have a wider potential window between the two. As shown in FIG. 6A, oxygen is generated at taC:N at about +2.2 V vs. SCE and hydrogen at about −1.4V vs SCE, giving a potential window $W(O-H)_{taC:N}$ (difference between hydrogen evolution potential and oxygen evolution potential) of about 3.6 V, whereas for B-diamond the oxygen and hydrogen potentials are about +1.8V and about −0.7V vs SCE, respectively, and thus the potential window for B-diamond $W(O-H)_{BD}$ is about 2.5 V in 1M $HClO_4$.

Figure 6B:
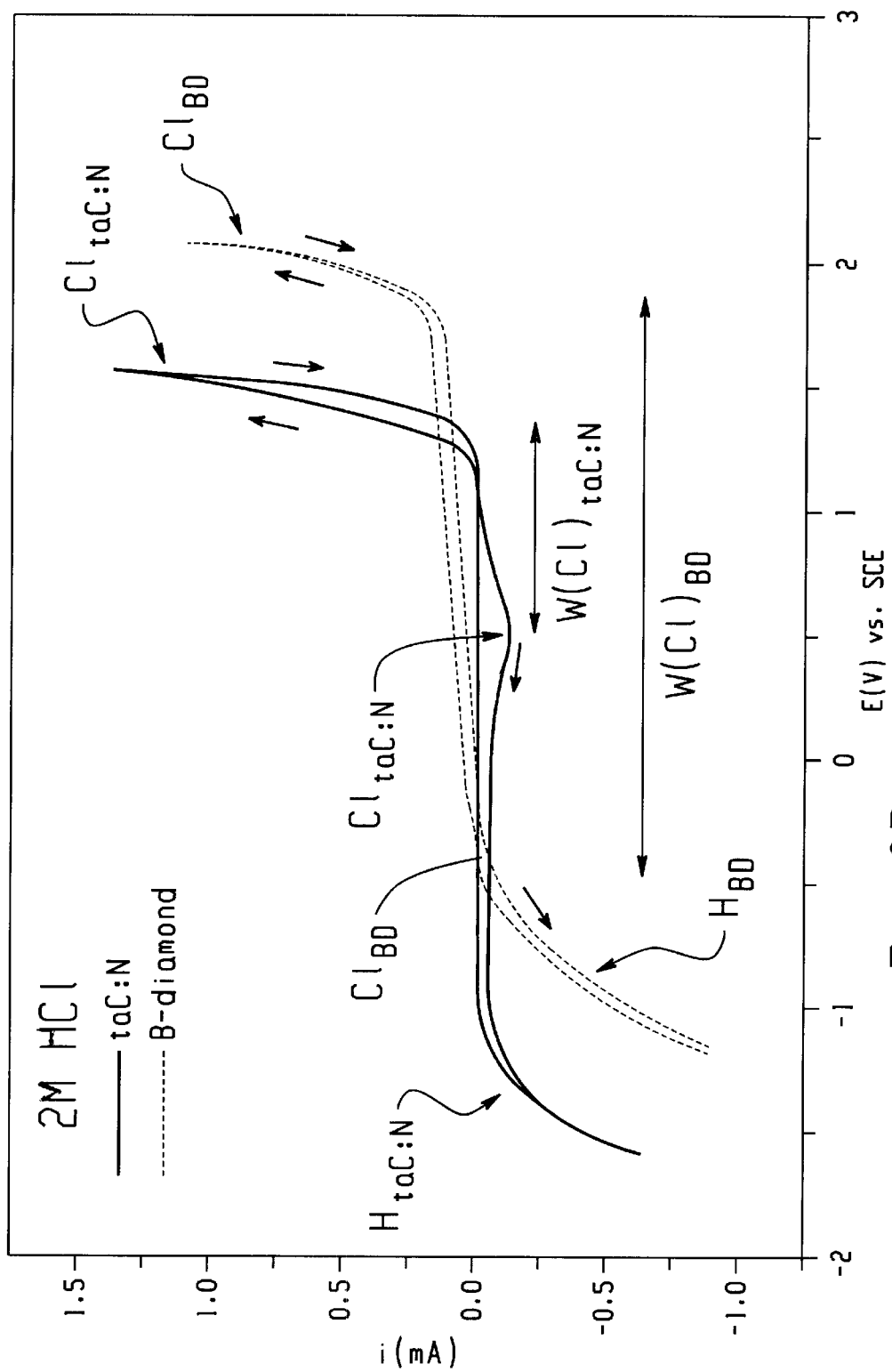
FIG. 6B is a plot of a cyclic voltammogram for stationary taC:N disks in 2M HCl at a scan rate of 100 mV/s in the directions of sweep shown.

However, the taC:N electrode anodic potential is lower than that of B-diamond with respect to chlorine evolution, as shown in FIG. 6b. The potential window $W(Cl)_{taC:N}$ with taC:N between the potentials for chlorine oxidation and reduction is about 0.7V, whereas the corresponding window $W(Cl)_{BD}$ is about 2.4V in 2M HCl. (The reactions taking place are $2Cl^- \rightarrow Cl_2 + 2e$ and its reverse for both B-diamond and taC:N.)

The rate of hydrogen and oxygen evolution is slower for taC:N than for B-diamond, as indicated by the larger overpotentials (potential which must be applied to drive the reaction) for both reactions in taC:N. That these rates are selectively very different for the taC:N and B-diamond systems is shown in FIG. 6B, where the comparative behavior in 2M HCl further indicates the higher hydrogen evolution potential $H_{taC:N}$ at taC:N, but now drastically lower anodic and cathodic overpotentials for the $Cl_2/Cl^-$ couple at taC:N, as indicated in the respective $W_{CL}$ values, 0.7 vs 2.4V.

The unexpected combination of slower reaction kinetics for taC:N with respect to hydrogen and oxygen than for boron-diamond, but much faster rates for the chlorine/chloride couple resulting from these observed differences in potential windows, is obviously valuable in electrosynthesis, for example for the selective generation of chlorine.

EXAMPLE 4

Rotating Ring Disk Electrode Studies of Efficiency of Chlorine Generation by taC:N and B-Diamond Electrodes in $HClO_4$ Experimental verification of the $Cl/O_2$ evolution contrast was obtained through product analysis by ring-disk electrode studies of the competition between the anodic processes. Rotating Ring Disk Electrode (RRDE) studies in 1M $HClO_4$ with varying concentrations of HCl show the greater efficiency of a taC:N disk in generating $Cl_2$, as compared with B-diamond.

Figure 7:
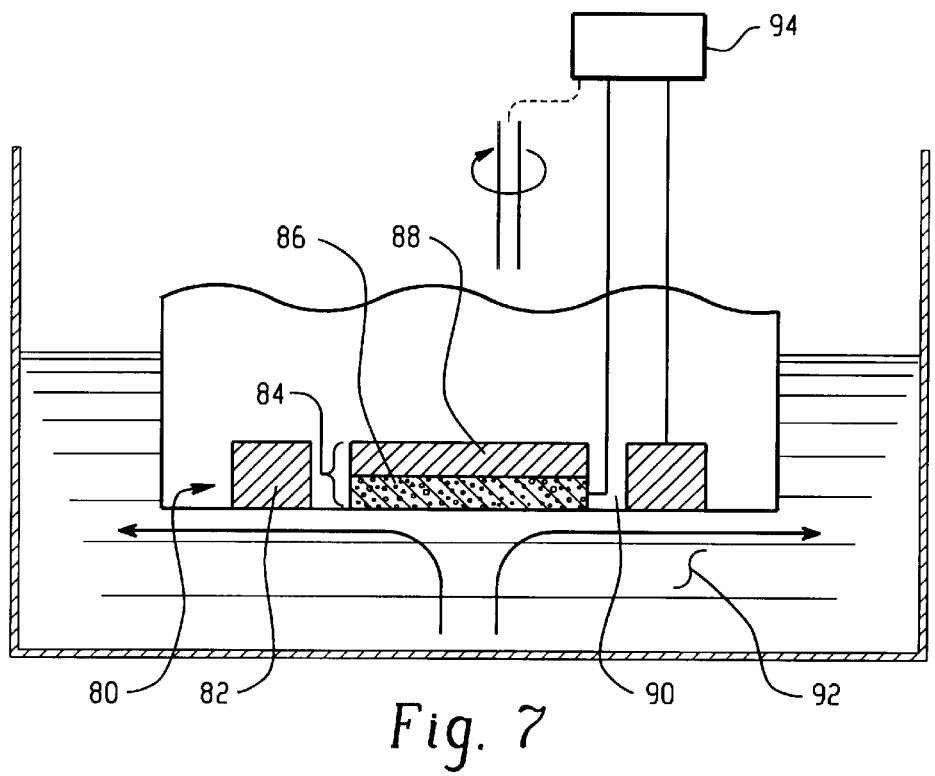
FIG. 7 is a side sectional view of a rotating ring disk electrode according to the present invention; and, FIG. 8 is a plot of collection efficiency relative to calibrated value in 1M $HClO_4$ against HCl added at taC:N and B-diamond rotating disks with Pt rings, respectively.

With reference to FIG. 7, RRDE electrodes 80 were prepared using a Pt, Au, or graphite ring 82 as a cathode in RRDE geometry spaced from taC:N or B-diamond coated disks 84, as an anode. The disks were prepared as for Example 1, with a layer 86 of taC:N or B-diamond on a silicon substrate 88. Epoxy sealing of gaps 90 and silver-epoxy contacts were used. To protect the thin taC:N film against damage, perfect planarity in the RRDE was not attempted. The collection efficiency was experimentally measured with a known couple, $Fe(CN)_6^{-3/-4}$.

Figure 8:
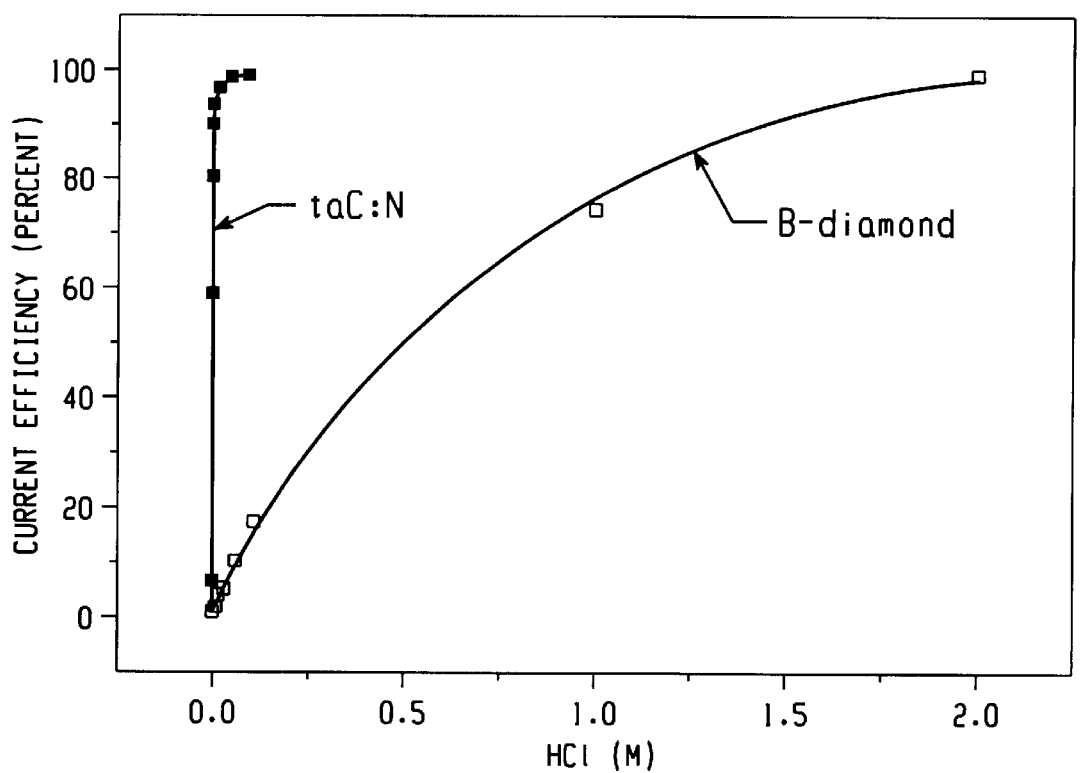

A systematic study using a platinum ring 82 with a 1M $HClO_4$ electrolyte 92 containing increasing concentrations of HCl is summarized in FIG. 8. A Pine MSRX controller and rotator 94 was used for the RRDE experiments. FIG. 8 shows the % current efficiency for $Cl_2$ evolution (the collection efficiency relative to the calibrated value for $Fe(CN)_6^{-3/-4}$) for taC:N and B-diamond rotating disks. In each case, the Pt ring potential (0.5 V vs. SCE) was held at the limiting current for $Cl_2 + 2e^- = 2Cl^-$ detection without oxygen reduction interference. The collection efficiency was determined from the linear ring current vs. disk current traces found in a positive-going potential sweep of the disk. Data was obtained with positive going potential sweeps at 10 mV/s, and 1600 rpm. Ring currents were monitored at 0.5V vs. SCE. Similar results were obtained with Au and graphite as the ring 82 material.

The value of the current efficiency is the ratio of the measured collection efficiency to that calibrated from $Fe(CN)_6^{-3/-4}$ for the taC:N and B-diamond RRDEs. This and previous RRDE studies show that B-diamond as an anode has a 100% current efficiency for chlorine generation (collection efficiency/calibrated value) only when the HCl concentration reaches about 2M. In contrast, the current efficiency for taC:N reaches 100% when only small amounts of HCl are present. FIG. 8 shows that no more than 50 mM of HCl is needed for 100% current efficiency for chlorine generation with taC:N in 1M $HClO_4$. At or above this concentration, the current efficiency is 100% over the range of HCl concentrations studied.

The results in FIG. 8 verify quantitatively the implications of FIG. 6B that a taC:N-based electrode shows high catalytic activity for chlorine generation.

EXAMPLE 5

Stability of taC:N Film Electrodes

To test the durability of taC:N for the chlorine evolution reaction, a stability test was performed on an electrode 22 with a 40 nm film 24 of taC:N, prepared as for Example 1. The test measured whether there was a damaging loss in carbon (through conversion to $CO_2$) from the film when a large amount of charge was passed through the film. The electrode was placed in 1M HCl at an anodic current density (charge passage) of 10 $mA/cm^2$. until an amount of charge was passed of $>10^4$ times the charge necessary to convert all carbon in the film, calculated conservatively at diamond density, to carbon dioxide at 4e/C-atom. The anode potential was continuously monitored and the current was interrupted periodically for cyclic voltammetry examination (as in FIG. 6B, solid line).

After passage of $1.03 \times 10^4$ times the $C \rightarrow CO_2$ coulombic capacity, the cyclic voltammetry of the taC:N electrode was unchanged from initial measurements. The potential under current was 1.96V vs. SCE, up only 0.13 V from the 0–1 hr value of 1.83 V. Consumption of the taC:N film was calculated as being <0.01% of the current at 10 $mA/cm^2$ in 1M HCl, i.e. virtually no taC:N is consumed during use of the electrode for chlorine generation at this rate of charge passage. This figure compares very favorably with an average consumption of graphite anodes in brine caustic/chlorine cells of about 3% of the current passed. Accordingly, it is expected that the taC:N electrode, when used as an anode in a cell for chlorine generation, will have a much longer service life than comparable, conventional graphite electrodes.

The invention has been described with reference to preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. An electrochemical system comprising:
   an electrode at which an oxidation or reduction reaction takes place including:
      a substrate, and
      a layer of a material deposited on the substrate, the layer consisting essentially of carbon and nitrogen, the layer having a nitrogen concentration of at least about 5 atomic %;
   an electrolyte in contact with the electrode; and
   a counter electrode.
2. The system of claim 1, wherein the electrode comprises an anode.
3. The system of claim 1, wherein the substrate material is a silicon wafer.
4. The system of claim 1, wherein the layer is from about 10 nanometers to about 70 nanometers in thickness.
5. The system of claim 4, wherein the layer is from 30–50 nanometers in thickness.
6. An electrochemical system comprising:
   an electrode including:
      a substrate, and
      a layer of a material on the substrate, the layer being primarily nitrogen-incorporated tetrahedral carbon;
   an electrolyte in contact with the surface of the nitrogen-incorporated tetrahedral carbon layer; and
   a counter electrode.
7. The system of claim 6, wherein the layer has a nitrogen concentration of from about 5–15 atomic %.
8. The system of claim 1, wherein the layer has a nitrogen concentration of 8–12 atomic %.
9. The system of claim 2, further including:
   a cathode, and wherein the system is capable of being used for one of detection and synthesis of at least one of the group consisting of:
      i) a reaction involving a $Cl^-/Cl_2$ couple,
      ii) a reaction involving a couple selected from the group consisting of a quinone/hydroquinone couple, other catechol derivatives, and combinations thereof;
      iii) a reaction involving an outer sphere couple;
      iv) a reaction involving one of hydrogen evolution and oxygen evolution.

10. A chlorine generation system comprising:
   an electrode including:
   a substrate, and
   a layer of a material on the substrate, the layer consisting essentially of carbon and nitrogen, the layer having a nitrogen concentration of from about 5–15 atomic %;
   an electrolyte in contact with the layer, the electrolyte including chloride ions, chlorine being generated at the electrode; and
   a counter electrode.

11. The system of claim 1, wherein the layer of material is in the form of an array on the substrate.

12. An electrochemical system comprising:
   an electrode including:
   a substrate, and
   a layer of a material on the substrate, the layer consisting of carbon and nitrogen, the carbon having an atomic ratio of $sp^3/sp^2$ of from about 70/30 to about 85/15;
   an electrolyte in electrical contact with the layer; and
   a counter electrode.

* * * * *